United States Patent
Sweeney

(10) Patent No.: US 8,472,020 B2
(45) Date of Patent: Jun. 25, 2013

(54) PROCESS FOR ENHANCING DYE POLYMER RECORDING YIELDS BY PRE-SCANNING COATED SUBSTRATE FOR DEFECTS

(75) Inventor: Thomas I. Sweeney, Jermyn, PA (US)

(73) Assignee: Cinram Group, Inc., Phoenix, AZ (US)

( * ) Notice: Subject to any disclaimer, the term of this patent is extended or adjusted under 35 U.S.C. 154(b) by 1370 days.

(21) Appl. No.: 11/057,941

(22) Filed: Feb. 15, 2005

(65) Prior Publication Data

US 2006/0181706 A1    Aug. 17, 2006

(51) Int. Cl.
  *G01N 21/00*    (2006.01)
  *G11B 7/24*    (2006.01)

(52) U.S. Cl.
  USPC ............... 356/337; 430/270.15; 430/945

(58) Field of Classification Search
  None
  See application file for complete search history.

(56) References Cited

U.S. PATENT DOCUMENTS

| | | | |
|---|---|---|---|
| 3,317,736 A * | 5/1967 | Herrick et al. ............... 356/430 |
| 3,813,173 A * | 5/1974 | Teter ............... 356/239.7 |
| 4,336,545 A | 6/1982 | Howe et al. |
| 4,364,986 A | 12/1982 | Zwanenburg et al. |
| 4,825,430 A | 4/1989 | Halter et al. |
| 4,865,445 A * | 9/1989 | Kuriyama et al. ............... 356/73 |
| 5,002,455 A * | 3/1991 | Kuriyama et al. ......... 198/339.1 |
| 5,096,563 A * | 3/1992 | Yoshizawa et al. ............. 205/68 |
| 5,297,129 A | 3/1994 | Wilkinson et al. |
| 5,726,756 A * | 3/1998 | Aki et al. ............... 356/630 |
| 5,863,411 A * | 1/1999 | Kang et al. ............... 205/645 |
| 6,570,840 B1 | 5/2003 | Wilkinson et al. |
| 6,785,221 B2 | 8/2004 | Wilkinson et al. |
| 7,325,287 B2 | 2/2008 | Sweeney |
| 7,419,045 B2 | 9/2008 | Kelsch |
| 7,535,806 B2 | 5/2009 | Fumanti |
| 7,564,771 B2 | 7/2009 | Sweeney |
| 2003/0147326 A1* | 8/2003 | Wilkinson et al. ......... 369/59.25 |
| 2003/0193875 A1 | 10/2003 | Rilum et al. |
| 2005/0061247 A1* | 3/2005 | Shibata et al. ............... 118/719 |
| 2006/0023598 A1 | 2/2006 | Babinski et al. |
| 2006/0101634 A1 | 5/2006 | Sweeney |
| 2006/0104190 A1 | 5/2006 | Babinski |
| 2006/0165419 A1 | 7/2006 | Musto |
| 2006/0222808 A1 | 10/2006 | Pickutoski et al. |
| 2006/0270080 A1 | 11/2006 | Rinaldi |
| 2006/0274617 A1 | 12/2006 | Musto et al. |
| 2007/0008861 A1 | 1/2007 | Fumanti |
| 2007/0014224 A1 | 1/2007 | Sweeney |
| 2007/0029167 A1 | 2/2007 | Kelsch |
| 2007/0090006 A1 | 4/2007 | Kelsch |
| 2007/0098947 A1 | 5/2007 | Mueller |

FOREIGN PATENT DOCUMENTS

| | | | |
|---|---|---|---|
| JP | 60-136044 | * | 7/1985 |
| JP | 61082346 | * | 4/1986 |
| JP | 04-363649 | * | 6/1991 |
| JP | 09-179985 | * | 7/1997 |
| JP | 2000-048365 | * | 2/2000 |
| JP | 2000-076713 | * | 3/2000 |
| WO | WO 94/23343 | | 10/1994 |

OTHER PUBLICATIONS

Wilkinson, Richard., "DVD Mastering Using Dye Polymer Media" Optical Data Storage Topical meeting, 1997.*
"High Density Photoresist Mastering".
"A Guide To Stamper Making".
"Cutting LBRs down to size", www.oto-online.com/nov00/cutting.html.
"Mastering Beyond DVD Densities".
"Ultra Violet—The Key to Successful DVD and CD Mastering".
U.S. Appl. No. 11/705,682, filed Feb. 13, 2007.
U.S. Appl. No. 11/715,249, filed Mar. 6, 2007.
U.S. Appl. No. 11/726,968, filed Mar. 22, 2007.
U.S. Appl. No. 11/705,682, filed Feb. 13, 2007 of Michael Parette.
U.S. Appl. No. 11/715,249, filed Mar. 6, 2007 of William R. Mueller et al.
U.S. Appl. No. 11/726,968, filed Mar. 22, 2007 of Lewis Gensel et al.
U.S. Appl. No. 11/936,625, filed Nov. 7, 2007 of Petrus Hubertus Van Hoof et al.
U.S. Appl. No. 11/938,572, filed Nov. 12, 2007 of Dominick A. Dallaverde et al.
U.S. Appl. No. 12/126,667, filed May 23, 2008 of Ed Pickutoski.

* cited by examiner

*Primary Examiner* — Cynthia Kelly
*Assistant Examiner* — Anna Verderame
(74) *Attorney, Agent, or Firm* — Cooper & Dunham LLP

(57) ABSTRACT

A method for enhancing recording yields by monitoring dye polymer formation on a glass substrate is provided. After the glass substrate is coated with a dye polymer layer and before pits are formed on the dye-polymer coated glass, the dye polymer coated glass substrate is scanned to detect defects. The dye-polymer coated glass is discarded on the one hand if the defects detected through the scanning are at or above an unacceptable threshold level, and on the other hand data is written on the dye-polymer coated glass if the defects detected through the scanning are below the unacceptable threshold level.

18 Claims, 4 Drawing Sheets

| Monthly | recording yield | scanner yield | DF Gain | DG Threshold |
|---|---|---|---|---|
| January | 80.1 | | | |
| February | 76.2 | | | |
| March | 77.1 | | | |
| April | 86 | 85 | 8 | 2 |
| May | 92.6 | 84 | 10 | 2 |
| June | 95.6 | 76 | 12 | 2 |
| July | 91.3 | 72 | 14 | 2 |
| August | 88.8 | 75 | 14 | 3 |
| September | 86 | 85 | 14 | 3 |
| October | 87 | 77 | 14 | 2 |
| November | 91.6 | 70 | 14 | 2 |
| December | 93 | 76 | 14 | 2 |

US 8,472,020 B2

PROCESS FOR ENHANCING DYE POLYMER RECORDING YIELDS BY PRE-SCANNING COATED SUBSTRATE FOR DEFECTS

TECHNICAL FIELD

This application relates to optical disc mastering which use dye polymer in place of photoresist. In particular, the application relates to a method for enhancing recording yields by monitoring dye polymer formation on glass substrate during the mastering process.

DESCRIPTION OF RELATED ART

Use of CDs (compact discs) and DVDs (digital versatile discs or digital video discs) as optical storage media ("optical discs") for storing and transporting content (such as audio, video, graphics, computer software, etc.) in an optically readable manner has been popular for a number of years.

Optical discs are conventionally available in several formats, including read-only formats such as CD-DA (digital audio compact disc), CD-ROM (CD-read-only memory), DVD-ROM, etc., and recordable formats in the form of (i) write-once read-many times formats such as CD-R (CD-recordable), and DVD-R (DVD-recordable), etc., or (ii) rewritable formats such as CD-RW (CD-rewriteable), DVD-RAM (DVD-Random Access Media), DVD-RW or DVD+RW (DVD-rewriteable), PD (Phase change disk) and other phase change optical discs. Optical disc players for these optical discs use a red laser. Optical discs using a blue laser have also been introduced, such as HD DVD and BD.

In conventional read-only type optical discs (for example, CD-ROM, DVD-ROM, etc.), data is generally stored as a series of "pits" embossed in a plane of "lands". Microscopic pits formed in a surface of a plastic medium are arranged in tracks, conventionally spaced radially from the center hub in a spiral track originating at the medium center hub and ending toward the medium's outer rim. The light reflected from a read-only medium's surface by an optical disc player or reader varies according to the presence or absence of pits along the information track. A photodetector and other electronics inside the optical disc player translate the signal from the transition points between these pits and lands caused by this variation into the 0s and 1s of the digital code representing the stored information.

Read-only type optical discs are produced by an injection molding process. Initially, data representing the content to be recorded, encoded as a run length limited digital code (commonly known as an EFM signal) which contains its digital information in the timing between transitions, is used to control a laser beam recorder to form pits in a photoresist or a dye-polymer layer (discussed below) on an optical grade glass disc known as a glass master. A metallized glass master is used in an electroforming process to form (typically, metal) stampers. A stamper is used on one side of an injection molding cavity to form a substrate of a transparent polymer, and the information bearing surface of the substrate is then covered with a reflective film or the like. In the case of a CD, a plastic coating is applied over the film, and then art (for example, a picture, a design, text, etc.) is typically printed on the upper surface of the disc, to form an end product. In the case of DVDs, two half-thickness substrates are bonded, with information layer(s) in the middle thereof, and the art is put on one of the outside surfaces.

Recordable type optical media typically include a spiral wobble groove in the substrate. The groove defines recording channels on the disc for recording data, provides information for tracking of the disc while writing or reading data, and has its wobble frequency modulated to contain addressing and other information necessary for the write and read processes. The substrate (incorporating the spiral wobble groove) can be formed by injection molding, using a stamper electroformed with a glass master. In addition, recordable-type optical media generally include a recording layer. Information is recorded in the recordable-type optical medium by directing a laser light beam modulated by signals to selectively change optical characteristics (reflectivity or extinction coefficient) of the recording layer. The recording layer in write-once read-many times optical media typically includes a photosensitive organic dye which is heated during recording to irreversibly to form a pattern of marks or pits into the recording layer.

Each recording side of a rewritable disc also uses multiple layers beginning with a polycarbonate plastic substrate containing a shallow spiral groove extending from the inside to the outside diameter of the disc. A DVD-RW disc additionally includes pits and lands on the areas between the coils of the groove (land pre-pits) and a DVD-RAM disc also inside the groove itself (land and groove). The substrates (incorporating the spiral groove, land pre-pits and embossed areas) may be formed by injection molding, using a stamper electroformed with a glass master. Next in the multiple layers of a rewritable disc typically comes a dielectric layer, followed by a phase-change type recording layer having a polycrystalline structure, another dielectric layer and a metal reflective layer. Additional layers may also be incorporated above or below the dielectric layer. During recording of the rewritable optical medium, the laser selectively heats tiny areas of the recording track to change the phase of each heated area from more crystalline into less crystalline (also known as "amorphous") phase, in order to create marks that can be called "pits". During erase, the laser (in a process called "annealing") changes the amorphous areas back into more crystalline areas.

As discussed above, glass masters (formed through a mastering process) can be used to electroform stampers for injection molding processes for forming read-only optical discs, recordable optical discs and/or rewritable optical discs. A glass master is typically created using one of two methods, a photoresist process or a dye-polymer process. The photoresist process is presently the more commonly employed. As discussed below (and see also U.S. Patent Application Publication No. US2003/0193875 A1, the contents of which are incorporated herein in its entirety by reference), each mastering process has its unique set of practical problems.

In the photoresist process, a liquid layer of photoresist is deposited (typically in spin coating process) onto a (cleaned and polished) glass substrate. The glass substrate with photoresist is then baked for a predetermined period of time (such as one half-hour). The data to be optically recorded is used to control a laser beam recorder to expose a latent image on the photoresist layer. After the image is exposed on the photoresist layer, a developing solution is deposited (for example, by spinning) onto the photoresist layer. The latent image on the photoresist washes away leaving pits of information. The developed glass master is then placed into a vacuum chamber and a small amount of a metal (typically, silver) is deposited, to form a metallized glass master.

The photoresist layer comprises a thin, photosensitive polymer resin layer of substantially uniform composition. A threshold quantity of light is required to initiate exposure at the photoresist surface. The extent and depth to which the photoresist below the immediate surface is exposed depends on the intensity and duration of the impinging write laser light and the optical characteristics of the photoresist material. When the photoresist is fully exposed through its entire thickness by a write beam of sufficient intensity (and then properly developed), flat-bottomed pits are produced. However, failure to fully expose (and/or properly develop) the photoresist resulting in improperly formed pits, such as containing residual photoresist at the bottom of the pit, generally causes noisy data output readings from replicated discs. In addition, the photoresist method of optical disc mastering has the additional complication that a chemical developing solution is used which requires careful handling, control and disposal. Many problems of the photoresist mastering process are discussed in International Publication No. WO 94/23343 (Reynolds), the contents of which are incorporated herein in its entirety by reference, in order to more fully describe the photoresist recording process as known to those skilled in the art as of the date of the invention described and claimed herein.

Unlike the photoresist method, dye-polymer recording is a thermal, self-developing mastering process, proceeding on the basis of physical principles quite different than those underlying the photoresist method. Dye-polymer recording is discussed in U.S. Pat. Nos. 4,336,545, 4,364,986, 4,825,430, 5,297,129, 6,570,840 and 6,785,221, the contents of which are incorporated herein in their entireties by reference, in order to more fully describe conventional dye-polymer recording processes as known to those skilled in the art as of the date of the invention described and claimed herein.

In the dye-polymer mastering process, a small amount of time is required, after the beam is activated at the beginning of each pit formation and as the disc master rotates, to heat the dye-polymer to its thermal threshold. On the other hand, cooling occurs almost instantly when the beam is shut off. However, unlike in the purely optical photoresist method, wherein virtually unmodified write pulses may be utilized for laser beam intensity modulation, dye-polymer disc mastering requires careful modification of the write pulses to counteract the thermal effects. While many adjustments of the parameters affecting the timing and geometry of the pits can be made, the interaction caused by making any adjustment that affects other parameters can be a tremendous problem which reduces yield and requires constant attention by a recording operator. Yield also can adversely be affected by defects (or roughness) in the dye-polymer layer. That is, defects in the surface of the dye polymer layer can cause noisy data readings, because playback signal amplitude is affected by surface characteristics. The mastering process can achieve more efficiency if a dye-polymer coated glass bearing an unacceptable level of defects is timely detected and removed from the process prior to any writing to the dye-polymer coated glass, thereby avoiding commitment of substantial efforts necessary to control writing to a defective dye-polymer coated glass.

SUMMARY

This application provides methods for enhancing recording yields by monitoring dye polymer formation on glass. A method for enhancing recording yields by monitoring dye polymer formation on glass, according to an exemplary embodiment, includes (a) coating a glass substrate with a dye polymer layer, (b) scanning the dye polymer coated glass substrate to detect defects, (c) discarding the dye-polymer coated glass without data written on the dye-polymer coated glass if the detected defects are at or above an unacceptable threshold level, and (d) writing data on the dye-polymer coated glass if the detected defects are below the unacceptable threshold level.

This application also provides an improvement to an automated mastering apparatus comprising (i) a cleaner and polisher for cleaning and polishing a glass substrate, (ii) a dye polymer coater for depositing a dye polymer coating on the glass substrate, (iii) an oven for baking the dye polymer coated glass substrate, and (iv) a controller for controlling components of the automated mastering apparatus. The improvement includes adding to the apparatus a scanner for scanning the dye polymer coated glass substrate to detect defects, and adapting the controller to control the components of the apparatus to discard the dye-polymer coated glass without data written on the dye-polymer coated glass if the defects detected by the scanner are at or above an unacceptable threshold level.

BRIEF DESCRIPTION OF THE DRAWINGS

The features of the present application can be more readily understood from the following detailed description with reference to the accompanying drawings wherein.

DETAILED DESCRIPTION

This application is directed to methods for enhancing recording yields by monitoring dye polymer formation on glass. Use of a dye polymer mastering process has many differences and advantages as compared to use of a photoresist-type mastering process, as, for example, discussed briefly above. As mentioned above, one example of a drawback of the photoresist-type mastering process is that a developing solution must be applied in a photoresist mastering process to develop a latent image formed in the photoresist layer. On the other hand, the dye polymer mastering process uses a thermal process and does not use chemical development. In addition, a direct-read-after-write (DRAW) process can be applied in dye polymer mastering. In the DRAW process, pits are cut in the dye polymer, pit quality is immediately checked in real time and, through a closed-loop control system, any needed adjustments are made to focus and laser power.

Figure 1:
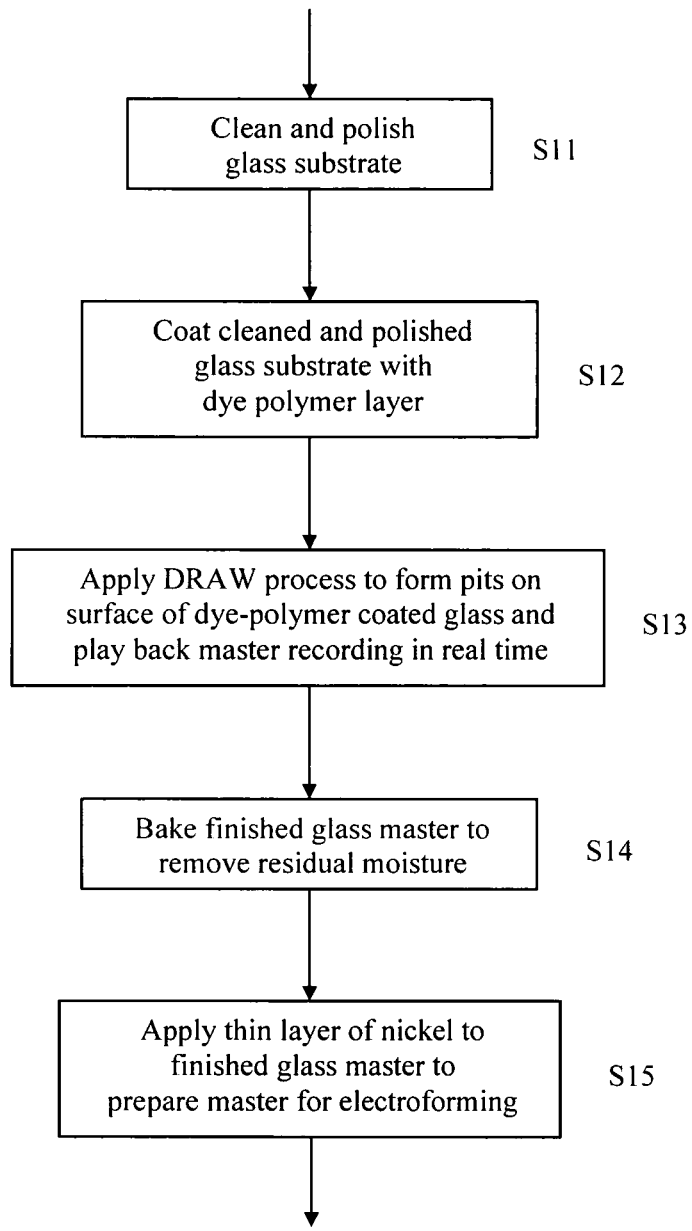
FIG. 1 shows a flow chart for a conventional dye polymer mastering process.

An exemplary dye polymer mastering process of a DRAW type will be explained with reference to FIG. 1. A glass substrate is cleaned and polished (step S11). Dye polymer is spin coated onto the cleaned and polished glass substrate (step S12). A DRAW process is applied with one or more laser sources to form pits on the surface of the dye-polymer coated glass substrate and play back the master recording in real time (step S13). The finished glass master is baked to remove residual moisture (step S14). A thin layer of nickel is applied to the glass master to prepare the master for electroforming (step S15). Alternatively, the glass can be baked prior to the DRAW process.

The real-time feedback and automatic adjustment of the DRAW process can enhance pit quality. However, even when the finished glass master has high pit quality, as mentioned above, yield can nevertheless be suboptimal if the dye polymer surface has an unacceptable level of defects. Suboptimal yield translates to wasted resources.

The term "defect" is used herein in its broadest sense to cover any deviation in physical property in a dye polymer coated glass substrate which would cause optical disc produced with stampers formed from the glass master to be (a) non compliant with the relevant standards (for example, CD, DVD, HD-DVD, BD, etc.) and/or (b) unplayable by a standards compliant optical disc player.

Figure 2:
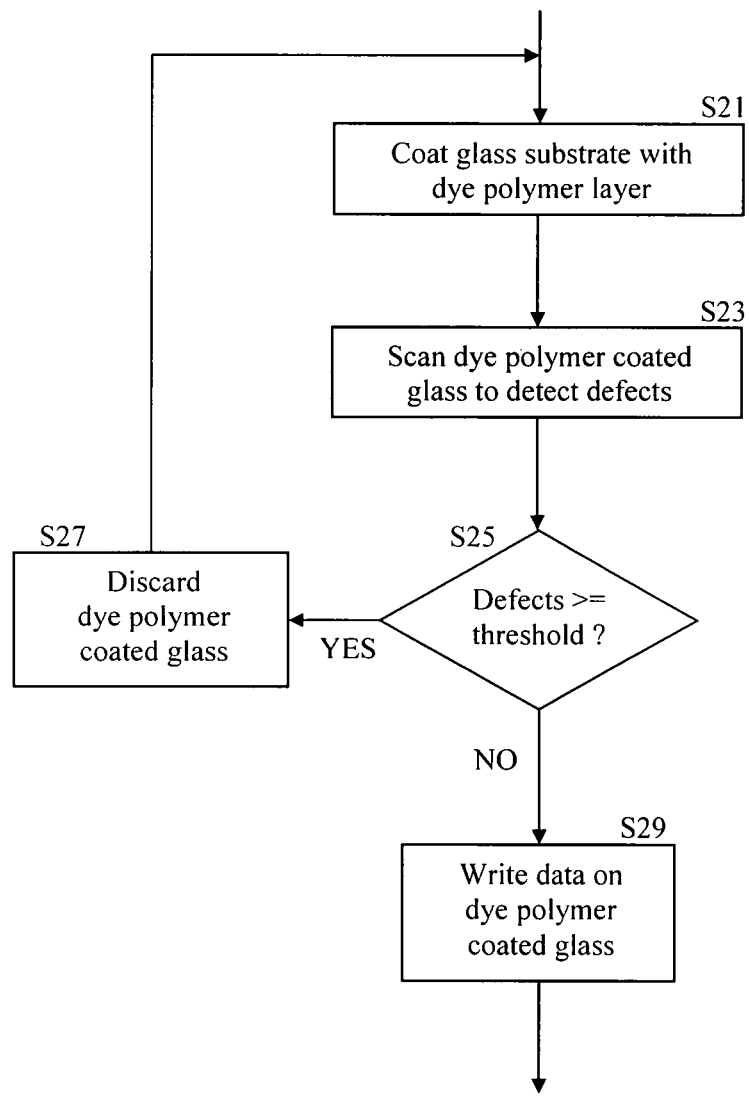
FIG. 2 shows a flow chart of a method for enhancing recording yields by monitoring dye polymer formation on glass, in accordance with an exemplary embodiment of the present application.

A method for enhancing recording yields by monitoring dye polymer formation on glass will now be explained with reference to FIG. 2. As with known dye polymer mastering processes, a glass substrate is coated (for example, via a spin coating process) with a dye polymer layer (step S21). The dye polymer covered glass is scanned to detect defects, without writing data on the dye-polymer coated glass (step S23). The detected defects are compared to an unacceptable threshold level (step S25). The dye-polymer coated glass without data written on the dye-polymer coated glass is discarded (step S27) and the process starts again with another glass substrate if the defects detected in step (b) are at or above the unacceptable threshold level (step S25, YES). Data is written on the dye-polymer coated glass (step S29) if the defects detected in step S23 are below the unacceptable threshold level (step S25, NO). In addition, the dye-polymer coated glass may be tested for defects a second time, for example, via DRAW playback, and unsatisfactory glass (that is, with unacceptable level of defects) written with data is also discarded.

The unacceptable threshold level may be determined through trial and error, and may depend in part on an acceptable percentage of recording yield. In other word, if 100% recording yield is desired (and assuming that it is possible to consistently achieve 100% yield), the unacceptable threshold will need to be set to a very low level which can be determined through experimentation. Practical considerations such as the cost of the glass substrate also may factor in many instances into the determination of an unacceptable threshold level. The unacceptable threshold level may be predetermined or may be selected by an operator prior to the step of determining whether to discard a dye polymer coated glass substrate.

The decision whether to discard a dye polymer coated substrate may also depend on a size of the defects. For example, in such a case, after the scanning step, a size of the defects detected through the scanning may be determined and then compared to an unacceptable size threshold. The dye-polymer coated glass without data written on the dye-polymer coated glass may be discarded if the size of the defects is greater than or equal to the predetermined unacceptable size threshold. The unacceptable size threshold may be predetermined or may be selected by an operator.

The decision whether to discard a dye polymer coated substrate may also depend on, for example, a percentage of the dye polymer surface occupied by the defects. The percentage of the dye polymer surface occupied by the defects may be determined concurrently with or after the scanning step and then compared to a predetermined unacceptable percentage threshold. The dye-polymer coated glass without data written on the dye-polymer coated glass can be discarded if the percentage of the dye polymer surface occupied by the defects is greater than or equal to a predetermined unacceptable percentage threshold. The unacceptable percentage threshold can be selected by an operator prior to scanning.

In addition to scanning for defects, the dye-polymer coated glass may be scanned to determine thicknesses at a plurality of locations of the dye polymer layer, and the thicknesses can be compared to a preprogrammed standard (for example, to determine whether the thicknesses fall within an acceptable range centered by the preprogrammed expected thickness). The dye-polymer coated glass without data written on the dye-polymer coated glass can be discarded if a percentage of the thicknesses at the plural locations of the dye polymer layer not within the preprogrammed standard is greater than or equal to a predetermined unacceptable percentage. Each of the predetermined expected thickness, the unacceptable percentage and the acceptable range can be selected by the operator.

Other steps may be included in the process. For example, the dye polymer coated substrate may be baked after or before scanning.

The method is preferably integrated in an automated mastering process. For example, transporting of the dye-polymer coated glass to the scanner may be an integrated step in the automated mastering process. As another example, the method may be implemented in a computer program stored on a computer readable medium and/or transmitted via a computer network or other transmission medium, and the program when running on a computer controls the components of an automated mastering system. A number of automated mastering systems are commercially available. For example, the Resist Master Preparation Line available from ODC Nimbus is an automated mastering system which implements a photoresist mastering process. The LaserPrep P-4000 is another automated mastering glass preparation system available from ODC Nimbus. The LaserPrep P-4000 implements a dye polymer mastering process, but does not perform prescanning and does not include a laser beam recorder (LBR) and metallizer.

Figure 3:
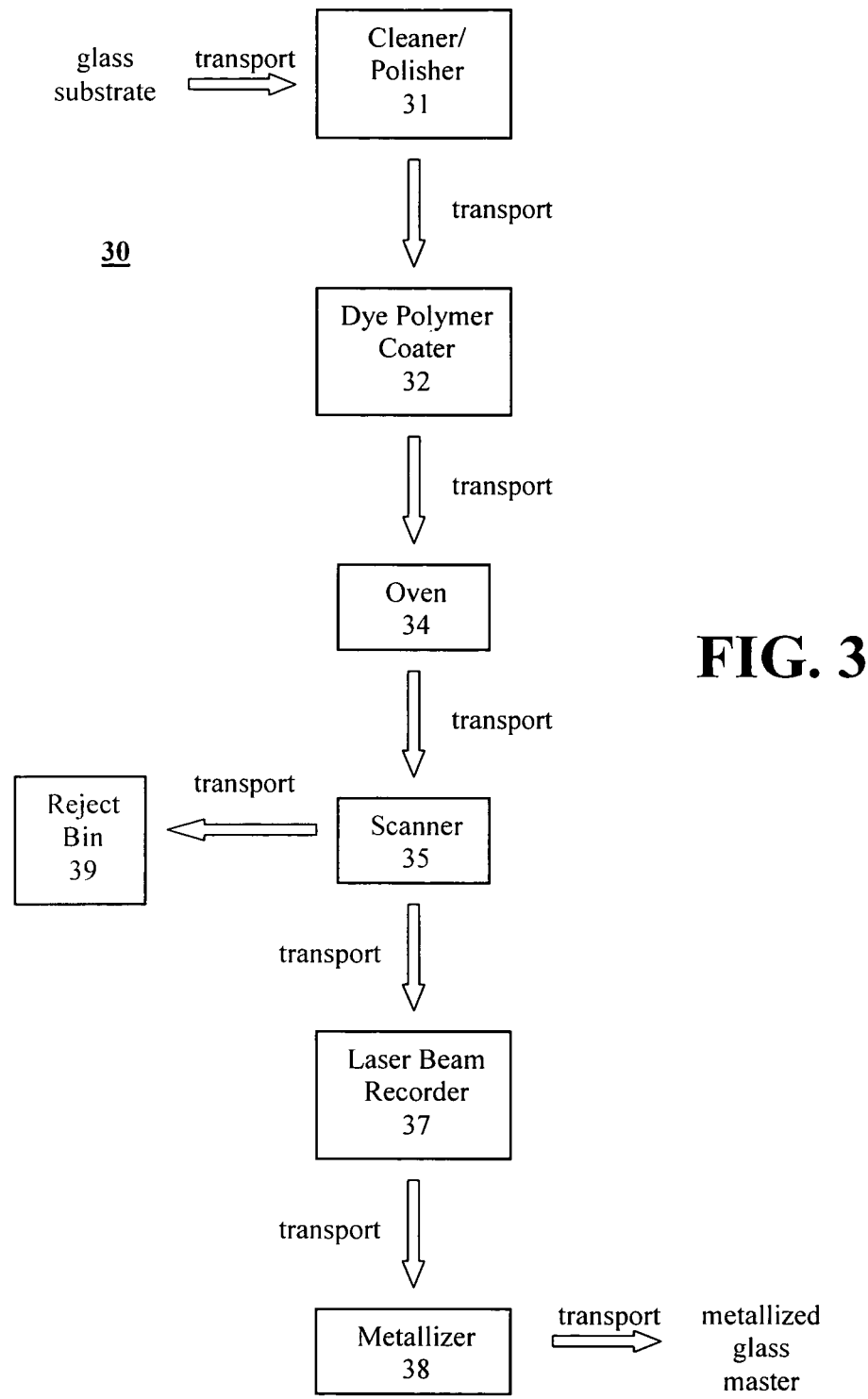
FIG. 3 shows a block diagram for an automated mastering system, according to an exemplary embodiment.

An automated mastering apparatus, according to an exemplary embodiment is shown in FIG. 3. Apparatus 30 includes a cleaner and polisher 31, a dye polymer coater 32, an oven 34, a scanner 35, an LBR 37, metallizer 38 and an optional reject bin 39 (which can be external to the apparatus). A glass substrate is supplied to the apparatus 30, by hand or by an automated mechanism (such as a cassette). Thereafter, the substrate is transported automatically from one component of the apparatus to another component of the apparatus. For example, the glass substrate is initially transported to the cleaner/polisher 31 which cleans and polishes the glass substrate. Next, the cleaned and polished glass substrate is transported to the coater 32 which deposits a coating (for example, by spin coating) of dye polymer on the glass substrate. The dye polymer coated glass substrate is transported to the oven 34 and baked for a period of time (for example, thirty minutes), and then transported to the scanner 35 which scans the dye polymer coated glass substrate for defects (for example, in manner discussed above). Alternatively, the dye polymer coated glass substrate is transported from the coater 32 to the scanner 35, scanned, and then transported to the oven 34 wherein it is baked. If the dye polymer coated glass substrate has an unacceptable level of defects, it is removed from the process and transported to the reject bin 39. On the other hand, if the dye polymer coated glass substrate has an acceptable level of defects (for example, none or below a predetermined threshold), the dye polymer coated glass substrate is transported to the LBR 37, and then data is written on the dye polymer coated glass. Next, the dye polymer coated glass bearing data is transported to the metallizer 38 which deposits a layer of metal (typically, nickel) on the dye polymer coated glass to produce a metallized glass master which is suitable for electroforming.

On the other hand, various steps in the methods of this disclosure may be performed by an operator. For example, the scanning may be performed by a scanner operated by the operator. As another example, whether the defects on the dye-polymer coated glass is at or above the unacceptable threshold level may be determined by the operator. In addition, the dye-polymer coated glass bearing defects at or above the unacceptable threshold level may be discarded by hand by the operator. Further, the dye-polymer coated glass may be transported to the scanner by hand by the operator.

The methods of this disclosure may be integrated in a process for manufacturing read-only type optical discs, recordable optical discs or rewritable optical discs.

The method may include applying a light beam to the dye-polymer coated glass without data written thereon, and measuring a light beam which passes through the glass substrate with the dye polymer layer. The applied light beam does not cause marks or pits to be formed in the dye polymer layer. The applied light beam does not change physical properties of the dye polymer coated substrate.

The methods of this application may be applied in a dye polymer mastering process to enhance recording yields. The efficacy of the methods was evident from tracking yield over a period of one year for a CD manufacturing line. Data representing yield over the one year time period is graphically and tabularly shown in FIGS. 4A and 4B, respectively. In the first three months of the year, a manufacturing process was applied without prescanning for defects in the dye polymer mastering process. The recording yields were satisfactory (80% or less) but not close to being optimal (for example, 90% or more). At the end of the third month, the manufacturing process was modified to include prescanning the dye-polymer coated glass in the dye polymer mastering process. Scan parameters were set by trial and error.

Figures 4A, 4B:
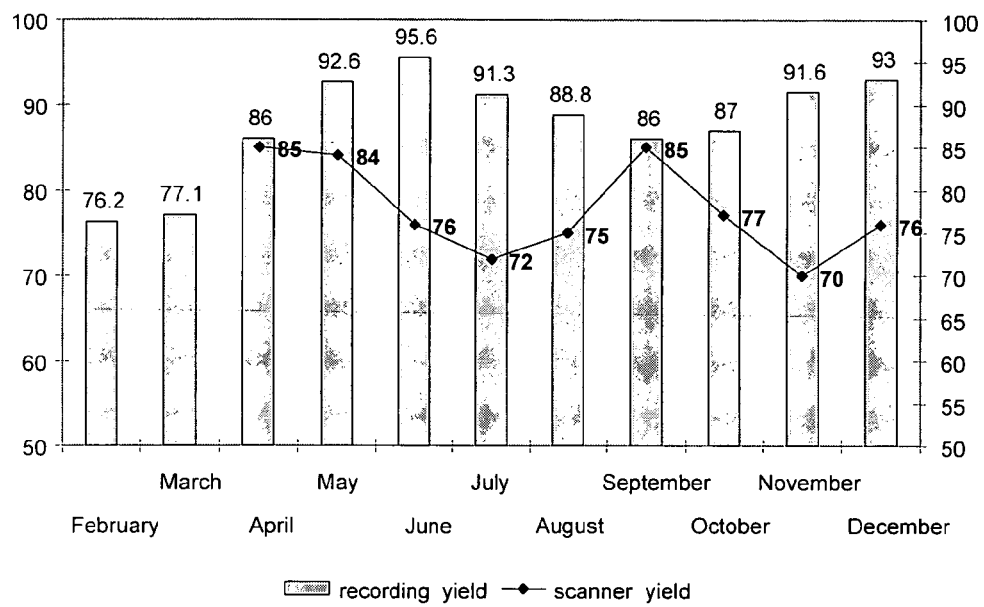
FIGS. 4A and 4B show a graphical view and a tabular view, respectively, of recording yield data collected over the course of a one-year time period.

FIG. 4B shows some of the scan parameters settings. DF (Dark Field) is a parameter that can be used to determine the presence of defects on/in the dye polymer covered glass. When the scanner's laser light encounters a defect, the light striking the dye polymer covered glass is scattered. The deflected light then hits the DF detector within the scanner head assembly. The more severe the imperfection (for example, larger, sharper angles) the more the light scatters and the greater the DF signal. DF Gain is a parameter used to intensify the DF signal returned from the DF detector. DF Threshold is a limit at which the glass is determined to be a failure. For example, if the DF Threshold is set to 4, a DF signal greater than 4 causes the glass to fail.

Initially, prescanning resulted in detection of few defective dye-polymer coated glass (that is the scanner yield was relatively high). However, as scan parameters were refined over time, more defective dye polymer coated glass were detected and discarded, thereby causing recording yield to improve and exceed the target level (90%).

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

For example, as noted above, the monitoring of dye polymer formation on glass and prescanning of the dye-polymer coated glass in the dye polymer mastering process can be supplemented by other tests for defect during the mastering process as well as additional tests in the manufacturing process that would tend to enhance yield.

What is claimed is:

1. A method for enhancing yields in an optical recording media manufacturing process, by monitoring dye polymer formation on glass, said method comprising the steps of:
    (a) coating a glass substrate with a dye polymer layer;
    (b) scanning the dye polymer coated glass substrate to detect defects;
    (c) discarding the dye polymer coated glass without data written on the dye-polymer coated glass if the defects detected in step (b) are at or above an unacceptable threshold level; and
    (d) writing data on the dye polymer coated glass if the defects detected in step (b) are below the unacceptable threshold level and utilizing the dye polymer coated glass bearing the data in said optical recording media manufacturing process,
    wherein said scanning in step (b) occurs prior to writing to the dye polymer coated glass, and
    wherein the scanning in step (b) does not cause marks or pits to be formed in the dye polymer layer, and does not change physical properties of the dye polymer coated substrate.

2. The method of claim 1 further comprising the step of:
    determining between steps (b) and (c) a size of the defects detected in step (b),
    wherein the dye-polymer coated glass is discarded in step (c) without data written on the dye-polymer coated glass if the size of the defects is greater than or equal to a predetermined unacceptable size threshold.

3. The method of claim 2, wherein the unacceptable size threshold is selected by an operator prior to step (b).

4. A method for an optical recording media manufacturing process, said method comprising the steps of:
    (a) coating a glass substrate with a dye polymer layer;
    (b) scanning the dye-polymer coated glass substrate to detect defects;
    (c) discarding the dye-polymer coated glass without data written on the dye-polymer coated glass if the defects detected in step (b) are at or above an unacceptable threshold level;
    (d) writing data on the dye polymer coated glass if the defects detected in step (b) are below the unacceptable threshold level, and utilizing the dye polymer coated glass bearing the data in said optical recording media manufacturing process; and
    (e) determining between steps (b) and (c) a percentage of a surface of the dye polymer layer occupied by the defects detected in step (b),
    wherein said scanning in step (b) occurs prior to writing to the dye polymer coated glass, and
    wherein the dye-polymer coated glass is discarded in step (c) without data written on the dye-polymer coated glass if the percentage of the surface of the dye polymer layer occupied by the defects is greater than or equal to a predetermined unacceptable percentage threshold.

5. The method of claim 4, wherein the unacceptable percentage threshold is selected by an operator prior to step (b).

6. The method of claim 1 further comprising the steps of:
    (e) scanning the dye-polymer coated glass to determine thickness at a plurality of locations of the dye polymer layer;
    (f) comparing the thicknesses determined in step (e) to a predetermined expected thickness; and
    (g) discarding the dye-polymer coated glass without data written on the dye-polymer coated glass if a percentage of the thicknesses determined in step (e) not within the preprogrammed standard is greater than or equal to a predetermined unacceptable percentage threshold.

7. The method of claim 6, wherein the predetermined expected thickness is selected by an operator prior to step (f).

8. The method of claim 6, wherein the acceptable range is selected by an operator prior to step (g).

9. The method of claim 6, wherein the unacceptable percentage threshold is selected by an operator prior to step (g).

10. A method for an optical recording media manufacturing process, said method comprising the steps of:
   (a) coating a glass substrate with a dye polymer layer;
   (b) scanning the dye polymer coated glass substrate to detect defects;
   (c) discarding the dye-polymer coated glass without data written on the dye-polymer coated glass if the defects detected in step (b) are at or above an unacceptable threshold level;
   (d) writing data on the dye polymer coated glass if the defects detected in step (b) are below the unacceptable threshold level and utilizing the dye polymer coated glass bearing the data in said optical recording media manufacturing process;
   (e) applying a modulated light beam to the dye polymer layer on the glass substrate to form pits on the dye polymer layer; and
   (f) testing the dye-polymer coated glass for defects a second time, after the pits are formed on the dye-polymer layer in step (e),
   wherein said scanning in step (b) occurs prior to writing to the dye polymer coated glass.

11. The method of claim 1, wherein the unacceptable threshold level is selected by an operator prior to step (c).

12. The method of claim 1 further comprising the step of: baking the dye polymer coated substrate after step (a) and before step (b).

13. The method of claim 1, wherein said steps (a) through (c) are integrated in an automated mastering process.

14. The method of claim 1 further comprising the step of: transporting the substrate after step (c) and before step (d) to a laser beam recorder if the defects detected in step (b) are not at or above the unacceptable threshold level,
   wherein the data is written by the laser beam recorder on the dye polymer coated glass in step (d).

15. The method of claim 1, further comprising the steps of:
   (e) applying a modulated laser beam to the dye polymer layer to cut pits in the dye polymer layer
   (f) checking the quality of the pits cut in step (e), and
   (g) adjusting the application of the modulated laser beam according to the result of step (f) to enhance the quality of subsequently cut pits, wherein
   step (f) is immediately performed in real time as step (e) is performed.

16. The method of claim 1, further comprising the step of baking the dye polymer coated substrate after step (b) and before step (d).

17. The method of claim 16, wherein step (c) is performed before the baking step.

18. The method of claim 10, wherein step (f) is performed immediately and in real time as step (e) is performed.

* * * * *